US010724987B2

(12) United States Patent
Deierling et al.

(10) Patent No.: US 10,724,987 B2
(45) Date of Patent: *Jul. 28, 2020

(54) SENSOR CIRCUIT FOR CONTROLLING, DETECTING, AND MEASURING A MOLECULAR COMPLEX

(71) Applicant: Roche Sequencing Solutions, Inc., Pleasanton, CA (US)

(72) Inventors: Kevin Deierling, Pescadero, CA (US); Roger J. A. Chen, Saratoga, CA (US); David J. Fullagar, Los Gatos, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/977,312

(22) Filed: Dec. 21, 2015

(65) Prior Publication Data

US 2016/0266064 A1 Sep. 15, 2016

Related U.S. Application Data

(63) Continuation of application No. 14/591,690, filed on Jan. 7, 2015, now Pat. No. 9,290,805, which is a (Continued)

(51) Int. Cl.
*G01N 27/447* (2006.01)
*C12Q 1/6874* (2018.01)
(Continued)

(52) U.S. Cl.
CPC ....... *G01N 27/4473* (2013.01); *C12Q 1/6869* (2013.01); *C12Q 1/6874* (2013.01);
(Continued)

(58) Field of Classification Search
CPC ......... G01N 27/4473; G01N 27/44782; G01N 27/44791; G01N 33/48721; C12Q 1/6869; C12Q 1/6874; Y10T 436/11
See application file for complete search history.

(56) References Cited

U.S. PATENT DOCUMENTS 5,235,267 A 8/1993 Schoneberg
5,260,663 A 11/1993 Blades
(Continued)

FOREIGN PATENT DOCUMENTS

CN 101421616 4/2009
CN 103193189 7/2013
(Continued)

OTHER PUBLICATIONS

Thei, Federico, et al. "Parallel recording of single ion channels: A heterogeneous system approach." IEEE Transactions on Nanotechnology 9.3 (2010): 295-302.*
(Continued)

*Primary Examiner* — Robert J Eom
(74) *Attorney, Agent, or Firm* — Roche Sequencing Solutions, Inc.

(57) ABSTRACT

A device for controlling, detecting, and measuring a molecular complex is disclosed. The device comprises a common electrode. The device further comprises a plurality of measurement cells. Each measurement cell includes a cell electrode and an integrator electronically coupled to the cell electrode. The integrator measures the current flowing between the common electrode and the cell electrode. The device further comprises a plurality of analog-to-digital converters, wherein an integrator from the plurality of measurement cells is electrically coupled to one analog-to-digital converter of the plurality of analog-to-digital converters.

16 Claims, 12 Drawing Sheets

Related U.S. Application Data continuation of application No. 13/777,879, filed on Feb. 26, 2013, now Pat. No. 8,986,629.

(60) Provisional application No. 61/603,782, filed on Feb. 27, 2012.

(51) Int. Cl.
*C12Q 1/6869* (2018.01)
*G01N 33/487* (2006.01)

(52) U.S. Cl.
CPC . *G01N 27/44782* (2013.01); *G01N 27/44791* (2013.01); *G01N 33/48721* (2013.01); *Y10T 436/11* (2015.01)

(56) References Cited

U.S. PATENT DOCUMENTS

| | | |
|---|---|---|
| 5,541,851 A | 7/1996 | Sato et al. |
| 5,747,805 A | 5/1998 | Youngquist |
| 6,014,213 A | 1/2000 | Waterhouse et al. |
| 6,217,731 B1 | 4/2001 | Kane et al. |
| 7,468,271 B2 | 12/2008 | Golovchenko et al. |
| 7,572,624 B2 | 8/2009 | Gumbrecht et al. |
| 9,605,307 B2 | 3/2017 | Chen |
| 9,869,655 B2 | 1/2018 | Chen |
| 2003/0080042 A1 | 5/2003 | Barth et al. |
| 2003/0102263 A1 | 6/2003 | Lopez et al. |
| 2004/0053337 A1 | 3/2004 | Yamazaki |
| 2004/0262636 A1 | 12/2004 | Yang et al. |
| 2005/0239134 A1 | 10/2005 | Gorenstein |
| 2006/0105373 A1 | 5/2006 | Pourmand |
| 2006/0246497 A1 | 11/2006 | Huang et al. |
| 2008/0094076 A1 | 4/2008 | Hibbs |
| 2009/0136958 A1 | 5/2009 | Gershow et al. |
| 2009/0233280 A1 | 9/2009 | Nomoto et al. |
| 2010/0078325 A1 | 4/2010 | Oliver |
| 2010/0261287 A1 | 10/2010 | Holt et al. |
| 2011/0008775 A1 | 1/2011 | Gao et al. |
| 2011/0168551 A1 | 7/2011 | White |
| 2011/0168968 A1 | 7/2011 | Yang et al. |
| 2011/0174625 A1 | 7/2011 | Akeson et al. |
| 2011/0218414 A1 | 9/2011 | Kamath et al. |
| 2012/0133354 A1 | 5/2012 | Canas et al. |
| 2013/0327644 A1 | 12/2013 | Turner et al. |
| 2014/0296083 A1 | 10/2014 | Brown et al. |
| 2014/0329693 A1 | 11/2014 | Reid et al. |
| 2015/0060276 A1 | 3/2015 | Golovchenko |

FOREIGN PATENT DOCUMENTS

| | | |
|---|---|---|
| EP | 1236807 | 11/1998 |
| EP | 1712891 | 10/2006 |
| JP | H06-186187 A | 7/1994 |
| JP | H07-198641 A | 8/1995 |
| JP | 2002195997 A | 7/2002 |
| JP | 2004333485 | 11/2004 |
| JP | 2005538377 | 12/2005 |
| JP | 2006-510881 A | 3/2006 |
| JP | 2008507703 | 3/2008 |
| JP | 2010502936 | 1/2010 |
| WO | WO-03095617 | 11/2003 |
| WO | WO-2007115694 | 10/2007 |
| WO | WO-2008079169 | 7/2008 |
| WO | WO-2009005547 | 1/2009 |
| WO | WO-2009047703 | 4/2009 |
| WO | WO-2009077734 | 6/2009 |
| WO | 2009138760 | 11/2009 |
| WO | WO-2010044932 | 4/2010 |
| WO | WO2010117470 A2 | 10/2010 |
| WO | WO2010122293 A1 | 10/2010 |
| WO | WO2010117470 A3 | 3/2011 |
| WO | 2011067559 A1 | 6/2011 |
| WO | 2011/097028 A1 | 8/2011 |
| WO | 2013011879 | 1/2013 |
| WO | 2013082619 | 6/2013 |

OTHER PUBLICATIONS

Wang, Gang, and William B. Dunbar. "An integrated, low noise patch-clamp amplifier for biological nanopore applications." Engineering in Medicine and Biology Society (EMBC), 2010 Annual International Conference of the IEEE. IEEE, 2010.*

Venkatesan et al., Nanopore Sensors for Nucleic Acid Analysis, Nature Nanotechnology, vol. 6, No. 10, pp. 615—Sep. 18, 2011.

Timp et al., Nanopore Sequencing: Electrical Measurements of the Code of Life, IEEE Transactions on Nanotechnology, vol. 9, No. 3, May 2010.

Rosenstein et al., Nanopore DNA Sensors in CMOS with On-Chip Low-Noise Preamplifiers, 2011 16th International Solid-State Sensors, Actuators and Microsystems Conference, Jun. 5-9, 2011.

Nakane et al., Nanopore Sensors for Nucleic Acid Analysis, Journal of Physics, Condensed Matter 15.32, Aug. 1, 2003, R1365.

Schuster et al., Self-Assembled α-Hemolysin Pores in an S-Layer-Supported Lipid Bilayer, Biochimica et Biophysica Acta 1370, (1998) 280-288.

Chen et al., Probing Single DNA Molecule Transport using Fabricated Nanopores, (Nano Lett, 2004, 4(11), pp. 2293-2298).

Axopatch 2008 Patch Clamp Theory and Operation, Mar. 1999 (Year: 1999).

Jiang et al. "Fabrication of sponge-like nanoporous platinum electrocatalysts for oxygen reduction through alloying and dealloying processes." Journal of University of Science and Technology of China. Jun. 30, 2008. vol. 38 No. 5. pp. 614-622.

Kumar, et al. PEG-labeled nucleotides and nanopore detection for single molecule DNA sequencing by synthesis. Sci Rep. 2012;2:684. Epub Sep. 21, 2012.

* cited by examiner

SENSOR CIRCUIT FOR CONTROLLING, DETECTING, AND MEASURING A MOLECULAR COMPLEX

CROSS REFERENCE TO OTHER APPLICATIONS

This application is a continuation of co-pending U.S. patent application Ser. No. 14/591,690, entitled SENSOR CIRCUIT FOR CONTROLLING, DETECTING, AND MEASURING A MOLECULAR COMPLEX, filed Jan. 7, 2015, which is a continuation of U.S. patent application Ser. No. 13/777,879, now U.S. Pat. No. 8,986,629, entitled SENSOR CIRCUIT FOR CONTROLLING, DETECTING, AND MEASURING A MOLECULAR COMPLEX, filed Feb. 26, 2013, which claims priority to U.S. Provisional Patent Application No. 61/603,782, entitled SENSOR CIRCUIT FOR CONTROLLING, DETECTING, AND MEASURING A MOLECULAR COMPLEX filed Feb. 27, 2012 all of which are incorporated herein by reference for all purposes.

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. It would be desirable to develop techniques for biochips that make them more robust, efficient, and cost-effective.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of 1 nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size. When a molecule, such as a DNA or RNA molecule, passes through the nanopore, it can partially or completely block the nanopore, causing a change in the magnitude of the current through the nanopore. It has been shown that the ionic current blockade can be correlated with the base pair sequence of the DNA or RNA molecule.

Figure 1:
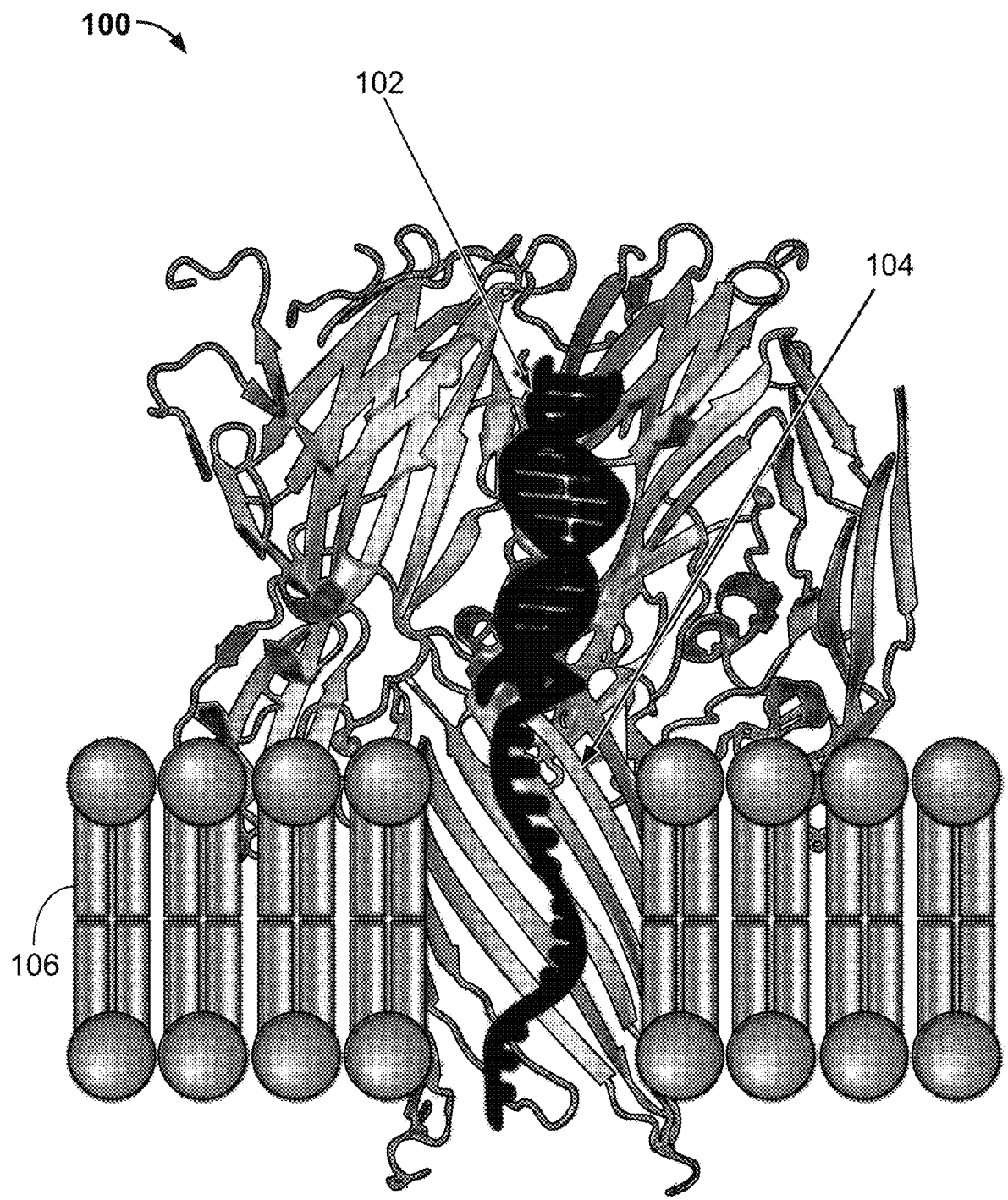
FIG. 1 illustrates a single stranded DNA (ssDNA) molecule constrained in a nanopore in a cell 100.

FIG. 1 illustrates a single stranded DNA (ssDNA) molecule constrained in a nanopore in a cell 100. As shown in FIG. 1, an anchored ssDNA molecule 102 is constrained within a biological nanopore 104 opening through an insulating membrane 106 (such as a lipid bilayer) formed above a sensor electrode.

A nanopore based sequencing chip incorporates a large number of autonomously operating sensor cells configured as an array. For example, an array of one million cells may include 1000 rows*100 columns of cells. This array enables the parallel sequencing of single stranded DNA (ssDNA) molecules by measuring the conductance difference between individual bases at the constriction zone of a nanopore entangled molecule. In some embodiments, non-linear (voltage dependent) conductance characteristics of the pore-molecular complex may be determined for distinguishing the specific nucleotide bases at a given location.

Figure 2:
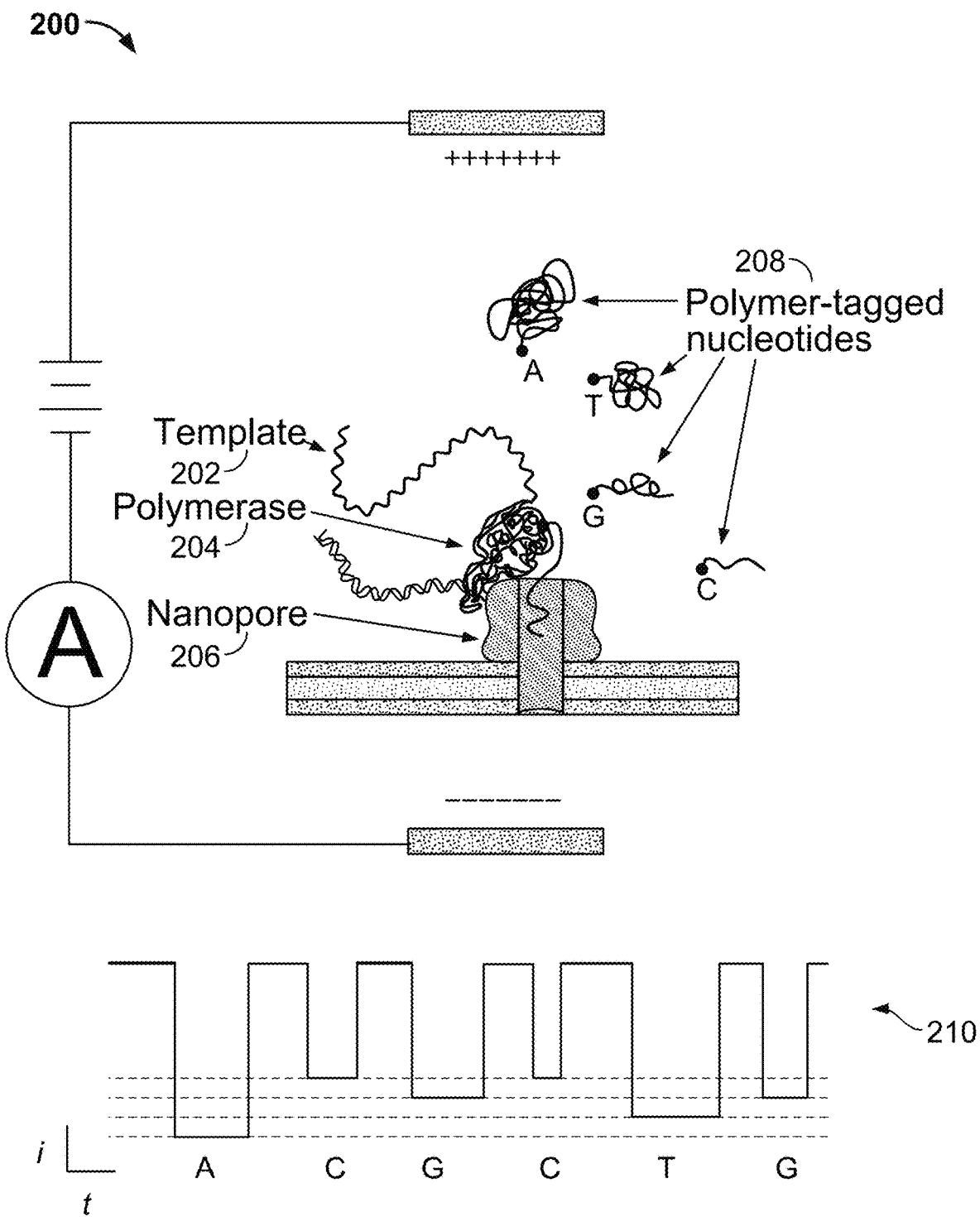
FIG. 2 illustrates an embodiment of a cell 200 performing nucleotide sequencing with the nanopore-based sequencing by synthesis (Nano-SBS) technique.

The nanopore array also enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the vestibule of nanopore 206. The tails of the tags can be modified to have strong affinity with the amino acid residues in the vestibule of nanopore 206. After polymerase catalyzed incorporation of the correct nucleotide, the tag-attached polyphosphate is released and will pass through nanopore 206 to generate a unique ionic current blockade signal 210, thereby identifying the added base electronically due to the tags' distinct chemical structures.

Figure 3:
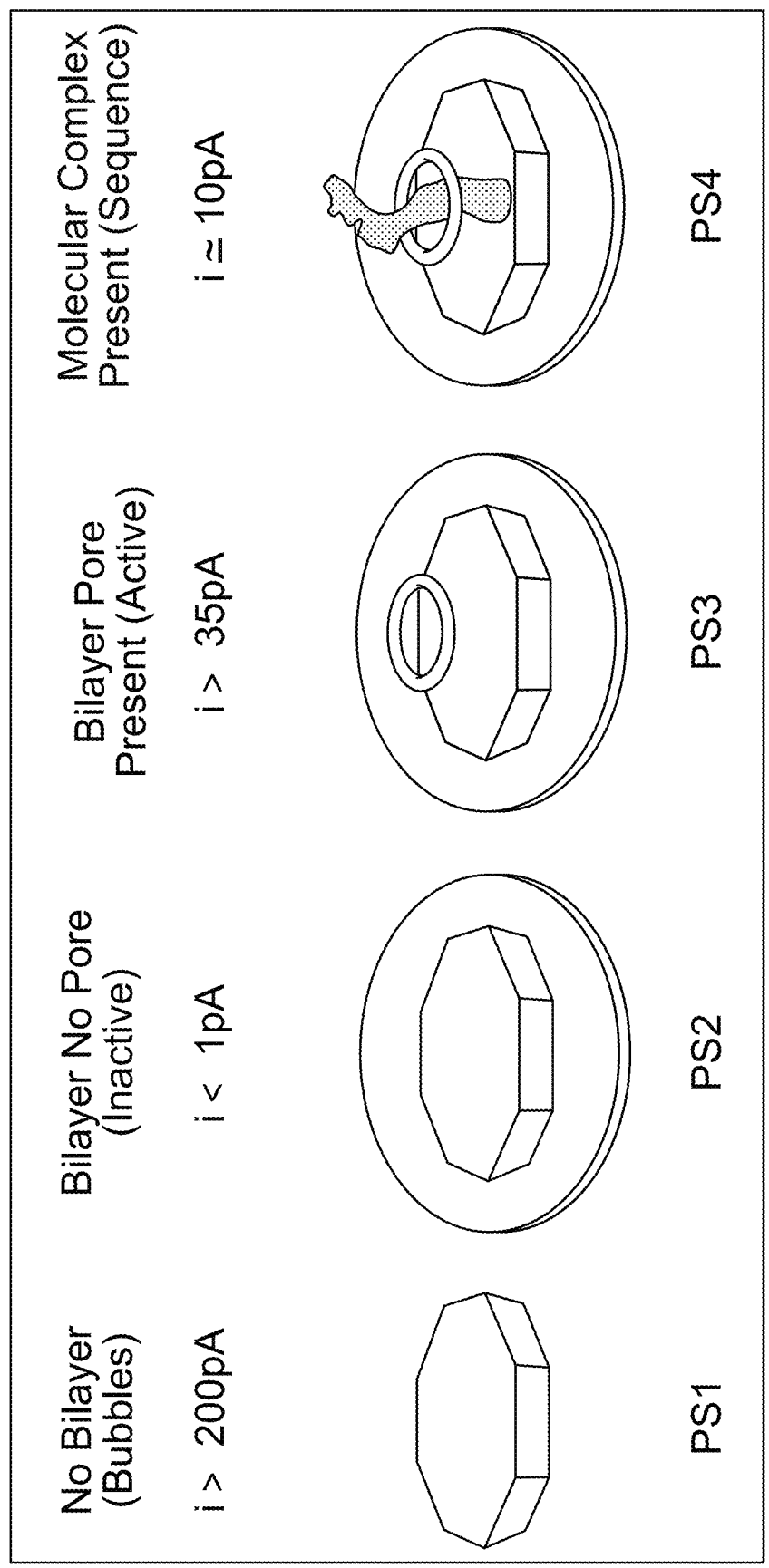
FIG. 3 illustrates four physical states of a sensor cell.

FIG. 3 illustrates four physical states of a sensor cell. The four physical states are hereinafter referred to as PS1-PS4. In the PS1 state, a cell has no lipid bilayer formed. In the PS2 state, a lipid bilayer has been formed but a nanopore on the lipid bilayer has not been formed yet. In the PS3 state, both a lipid bilayer and a nanopore have been formed. In the PS4 state, a molecule or a molecular complex (e.g., an ssDNA molecule or a tagged nucleotide) is interacting with the nanopore. After a sensor cell transits to the PS4 state, sequencing measurements may be obtained.

An electrode potential is applied to each cell in the array to move the physical state sequentially from PS1 to PS4. In some embodiments, four possible voltages may be applied to each of the cells in order to support the following transitions:

PS1→PS2
PS2→PS3
PS3→PS4
PSx→PSx (No transition)

In some embodiments, precise control of a piecewise linear voltage waveform stimulus applied to the electrode is used to transition the cells through different physical states.

The physical state of each cell can be determined by measuring a capacitance. In addition, the physical state can be determined by measuring a current flow when a bias voltage (e.g., ~50-150 mV) is applied.

In some embodiments, the electrode voltage potential is controlled and the electrode current is monitored simultaneously. In some embodiments, each cell of the array is controlled independently from others depending on the physical state of the cell. The independent control of a cell facilitates the management of a large number of cells that may be in different physical states.

In some embodiments, circuit simplification and circuit size reduction is achieved by constraining the allowable applied voltages at any given time to two and iteratively transitioning the cells of the array in batches between the physical states. For example, the cells of the array may be initially divided into a first group with cells in the PS1 state and a second group with cells in the PS2 state. The first group includes cells that do not have a bilayer already formed. The second group includes cells that have already had a bilayer formed. Initially, the first group includes all the cells in the array and the second group includes no cells. In order to transition the cells from the PS1 state to the PS2 state, a lipid bilayer formation electric voltage is applied to the cells. Measurements (e.g., current or capacitance measurements) are then performed to determine whether lipid bilayers have been formed in the cells. If the measurement corresponding to a cell indicates that a lipid bilayer has been formed, then the cell is determined as having transitioned from the PS1 state to the PS2 state, and the cell is moved from the first group to the second group. Since each of the cells in the second group has a lipid bilayer already formed, the cells in the second group no longer need to have the lipid bilayer formation electric voltage further applied. Therefore, a zero volt bias may be applied to the cells in the second group in order to effect a null operation (NOP), such that the cells remain in the same state. The cells in the first group do not have lipid bilayers already formed. Therefore, the lipid bilayer formation electric voltage is further applied to the cells in the first group. Over time, cells move from the initial PS1 state to the PS2 lipid bilayer state, and the above steps are halted once a sufficient percentage of the cells are in the PS2 state.

Similarly, cells can be iteratively electro-porated until a sufficient percentage has transitioned from the PS2 state to the PS3 state or from the PS3 state to the PS4 state.

Figure 4:
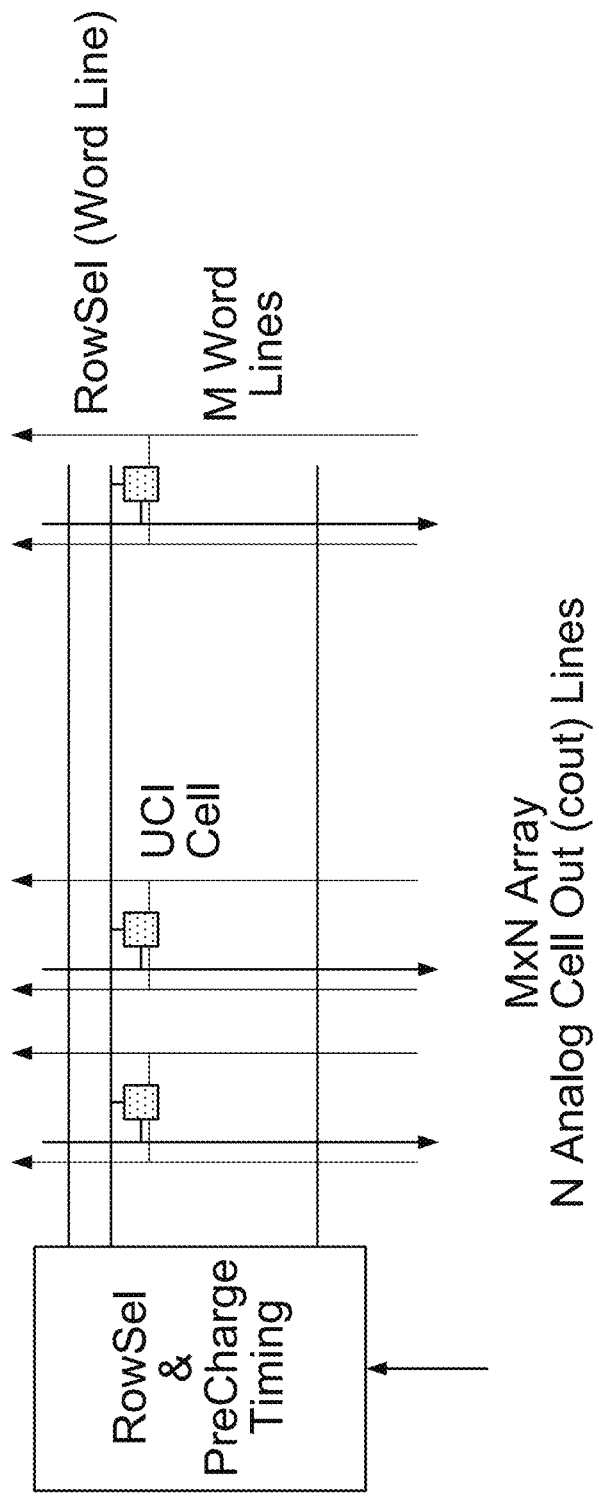
FIG. 4 illustrates an embodiment of a bank (M×N) of cells.

In some embodiments, the nanopore array is divided into banks of cells. FIG. 4 illustrates an embodiment of an M×N bank of cells. Row and column select lines are used to control the states of the individual cells. M and N may be any integer numbers. For example, a bank that is 8 k in size (referred to as a bank8k) may include 64×128 cells.

Figure 5:
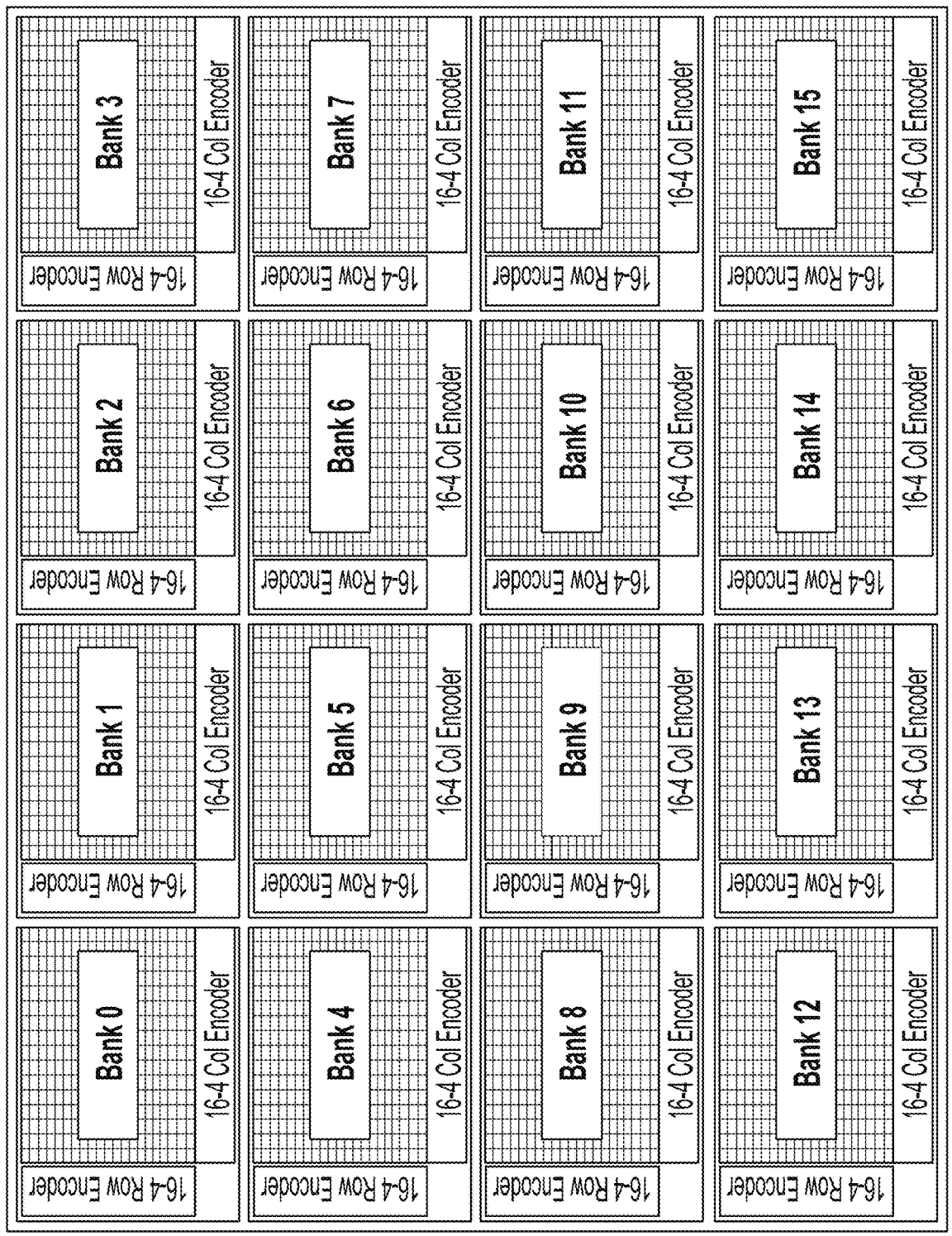
FIG. 5 illustrates a 128 k array implemented as sixteen bank8k elements.
Figure 6:
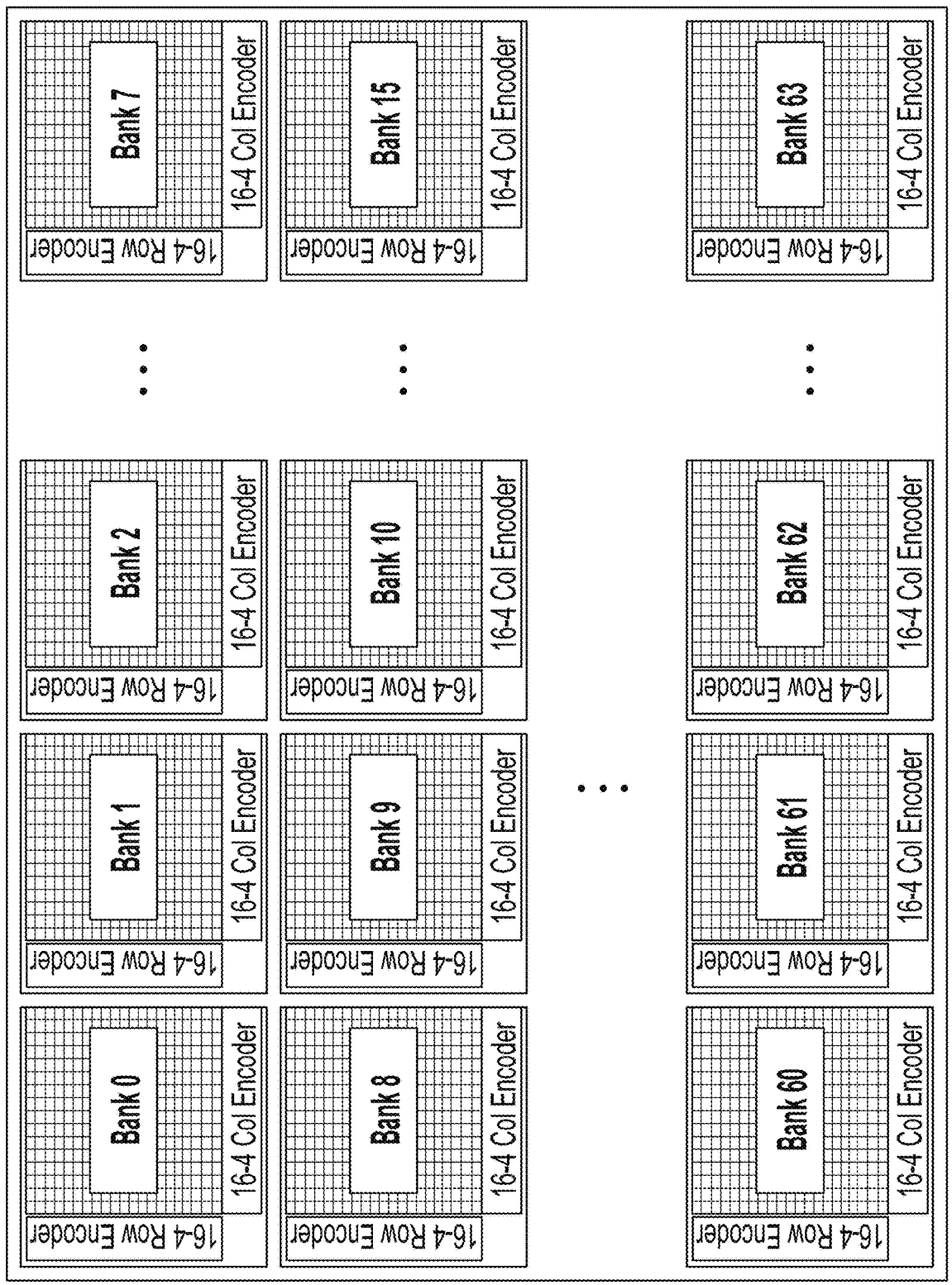
FIG. 6 illustrates a 512 k array implemented as an 8×8 array of bank8k elements.

Since each bank is autonomous, the nanopore array can be scaled by adding additional banks. For example, a 128 k array can be implemented as sixteen bank8k elements as shown in FIG. 5. A 512 k array can be implemented as an 8×8 array of bank8k elements as shown in FIG. 6. In some embodiments, the nanopore array may be scaled to include millions of cells. A small global control block may be used to generate control signals to select the banks and to set the cell applied voltage.

Figure 7:
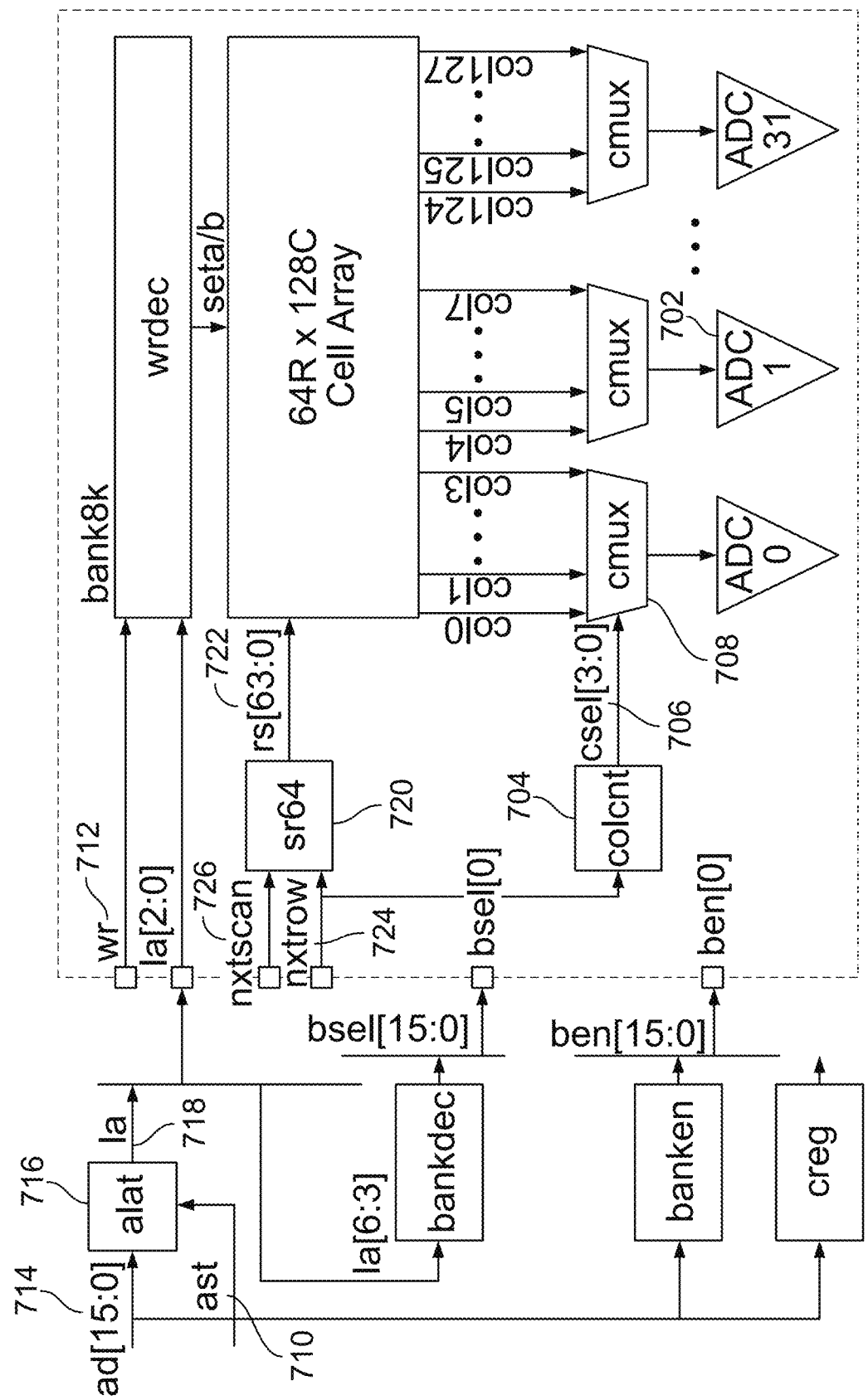
FIG. 7 illustrates an embodiment of a bank8k block.

FIG. 7 illustrates an embodiment of a bank8k block. The bank8k building block may be configured as 64 rows by 128 columns as shown in FIG. 7. Each bank8k block can be a complete sub-system with row and column addressing logic for reading/scanning, write address decoders, analog-to-digital converters (ADCs), and double buffered output.

In some embodiments, the read path and the write path of the bank8k block are separate and operate in a time multiplexed fashion. For example, a read is followed by a write. Each row is scanned by performing an analog-to-digital conversion of all of the cells in the row. Subsequently, software may optionally write a value to any cells in the same row in order to update the state, thereby selecting between two different applied voltages.

Each bank8k block incorporates eight ADCs 702 with each ADC 702 connected to 16 columns. A column counter (colcnt) 704 generates a 16 bit column select bus (csel) 706. The csel bus 706 controls eight separate 16:1 analog muxes 708 and selects which of the 16 columns is electrically connected to the ADCs 702. The ADC 702 outputs are latched into a register (not shown) that drive the low-voltage differential signal (LVDS) outputs. Note that the sequential cells read from a given row are physically located as col0, col16, . . . col112, col1, col17, . . . , and so on. The data is striped across the array with 16 bits. Similarly, the 16 bit data is written to the cells as:

d[0:7]→{col0, col16, . . . , col112}
d[8:15]~{col1, col17, . . . , col113}

In scan mode, all banks that are enabled are read out in parallel.

In some embodiments, scanning of a row requires reading 16 columns, with each column requiring 16 clock cycles. Thus, all cells in a row are read in 256 clocks, or 2 μs at a 128 MHz clock rate. The precharge period occurs immediately after a row has been scanned and lasts for 2 μs.

The bank8k is fully synchronous with all signals captured on the rising edge of the clocks, including ast 710, wr 712, and multiplexed address data bus 714 (ad[15:0]). During the first clock cycle, ad[15:0] is driven with the write address which is captured by the address latch 716 (alat) on the rising edge of the clock when address strobe 710 (ast) signal is high. Seven latched address (la) 718 bits are decoded to determine to which bank and word data is written. During the second clock cycle, ad[15:0] should be driven with the data and the wr 712 signal should be asserted high to indicate that this is a data write cycle. Thus, a normal write requires two cycles: the address cycle (indicated by the ast 710 signal), followed by the data cycle (indicated by the wr 712 signal).

There are three types of writes:
Bank Enable Register Write
Control Register write
Bank Cell AB Select Write
Some of the bits of the latched address 718, la[8:7], are used to determine the type of write, as shown in Table 1 below:

TABLE 1

| la[8:7] | Type of Write |
|---|---|
| 00 | Cell A/B Select |
| 01 | Bank Enable Register |
| 10 | Control Register |

The row select (rs) shift register 720 logic and the column counter 704 (colcnt) together operate to perform a raster scan of all the cells in the bank8k block. After a full integration period, a row is read out by asserting the row select 722 (rs) signal high. Together, the row select 722 and column select 704 enable a single cell to drive a given column. Eight columns within a row are read out in parallel, each connected to a different ADC. A selected cell drives the voltage on an integrating capacitor onto the column line using an in-cell source follower amplifier.

The row select logic is a 64 bit shift register (sr64 register 720) duplicated within every bank8k block. After all columns in a row have been read, an external FPGA (field-programmable gate array) may assert the nxtrow signal 724, which causes the sr64 register 720 to shift. Once the entire sub-windowed field has been scanned, the external FPGA asserts the nxtscan 726, which resets the sr64 register 720 back to row zero by shifting 1 bit into the first flip flop. By changing the period and the duration of the nxtrow 724 and nxtscan 726 signal, the array being scanned can be windowed, as will be described in greater detail below.

Precharging occurs on a row by row basis. A row goes into the precharge mode immediately after a row has been sampled by the ADCs. Each row has a flip flop that samples the row_enable signal when nxtrow 724 signal is asserted.

In addition, the row select shift register 720 is also used to generate the row precharge signal by connecting the $n^{th}$ precharge signal to the $(n+1)^{th}$ row select signal:

$Pre[n]=rs[n+1]$

A row is precharged during the row scanning period immediately after it has been read. This bit shifted precharge connection is implemented as a modulo 64 operation, and thus precharge[63] is logically connected to rs[0].

Figure 8:
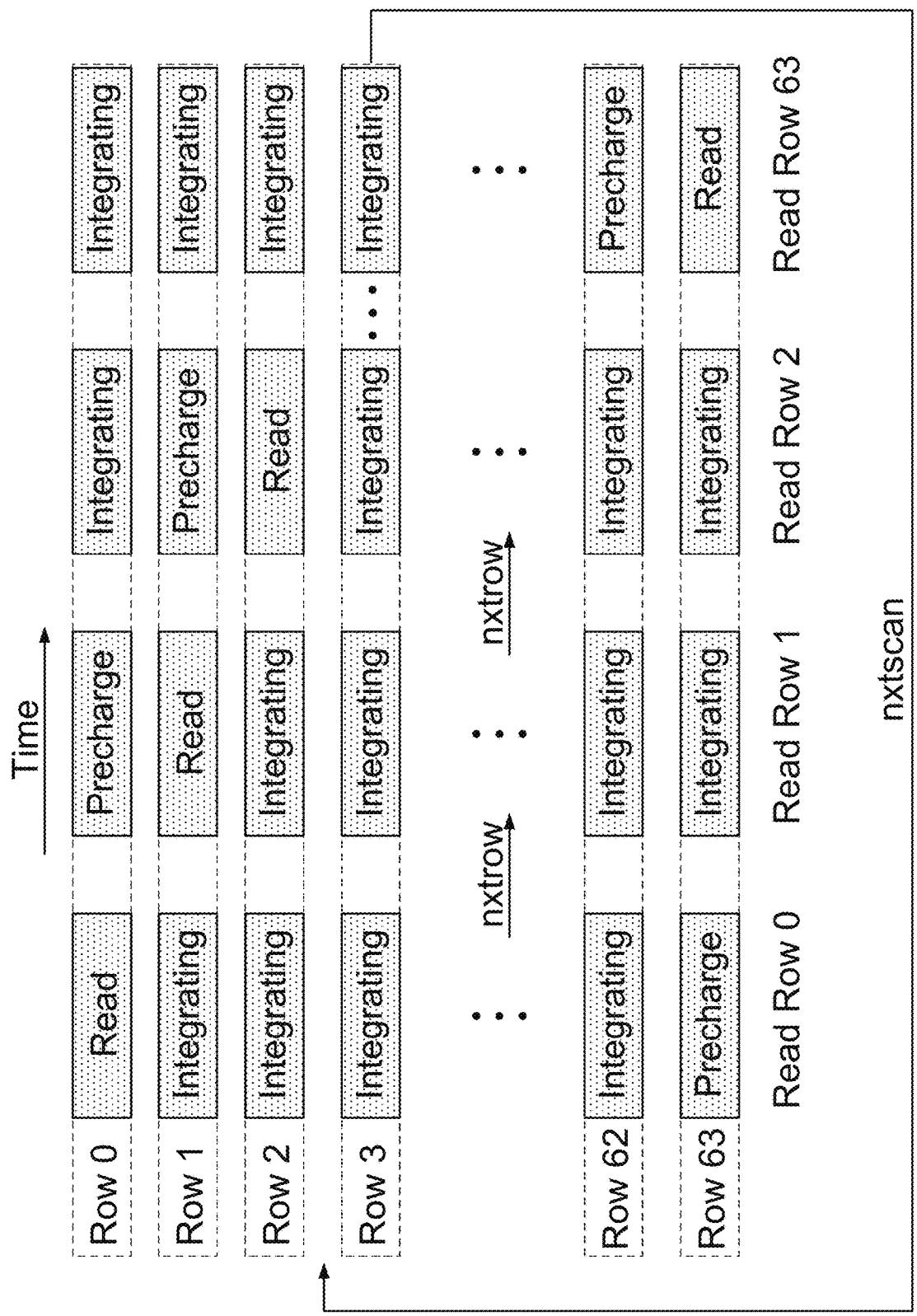
FIG. 8 illustrates an embodiment of a scan sequence.

FIG. 8 illustrates an embodiment of a scan sequence. After all 64 rows have been read (along with any intervening writes), the nxtscan signal is asserted to restart the scanning process at row 0.

Figure 9:
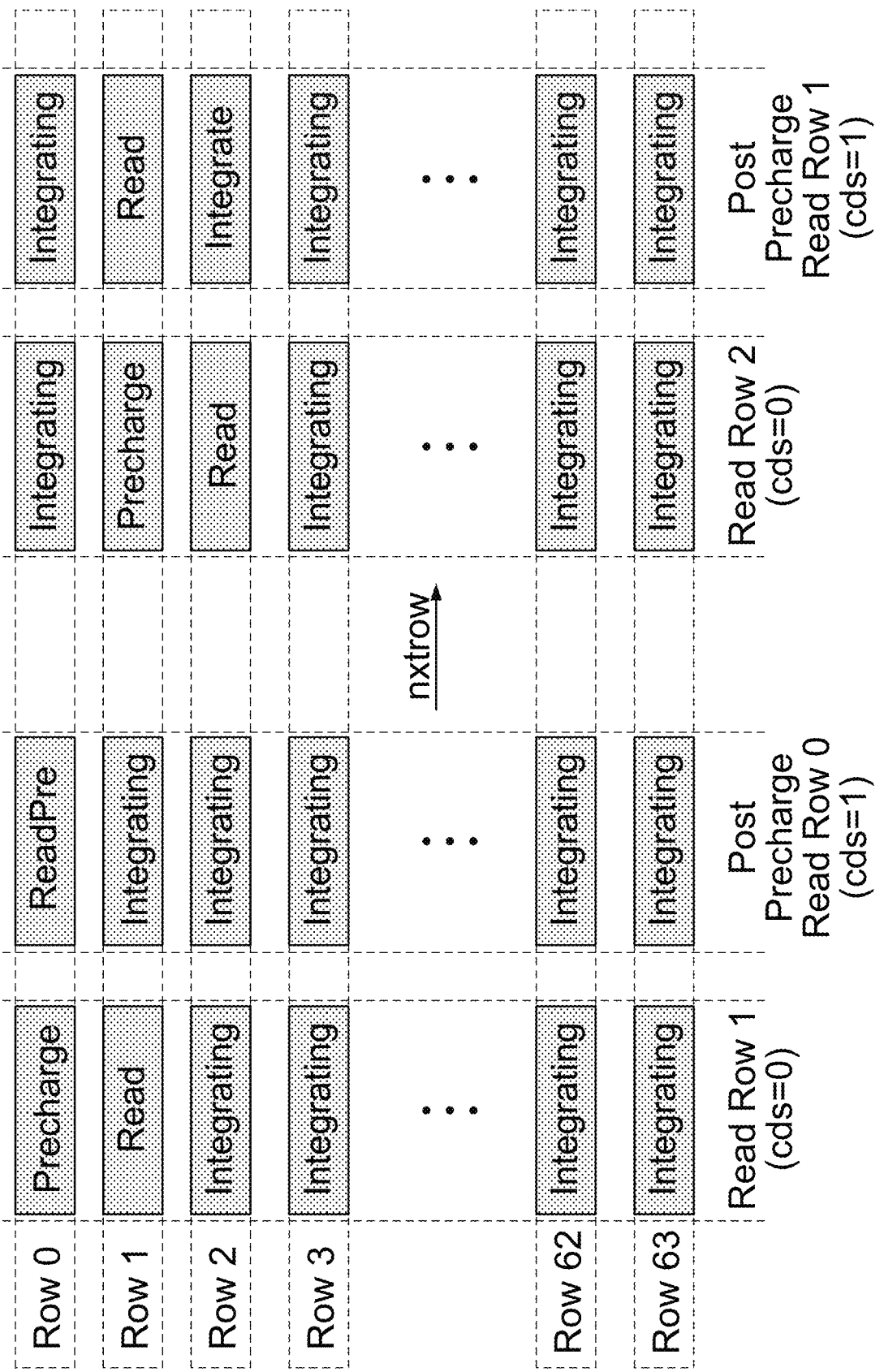
FIG. 9 illustrates an embodiment of a scan sequence.

FIG. 9 illustrates an embodiment of a scan sequence. Correlated double sampling (CDS) is enabled by asserting a CDS pin. In a normal measurement mode without CDS, the voltage on the capacitor is measured, and subsequently the nxtrow pin is asserted so that the next row can be read. Row N is pre-charged while Row N+1 is being read. Thus, a row is reset immediately after it has been read. Asserting the CDS pin allows the row that has just been precharged to be read. Thus, the value of the reset voltage can be read immediately after precharging is done and subsequently read again at a later time. By subtracting the two measurements, the kT/C thermal noise of the precharge transistor 1114 is reduced. In addition, charge sharing voltage divider effects between the integrator capacitance and the active follower in the cell are also reduced. Note that when correlated double sampling is performed, the effective measurement rate is reduced by half, since two ADC conversions are required for each integrated current measurement.

The row and column addresses are controlled by the nxtrow 724 and nxtscan 726 signals. Asserting the nxtrow 724 input high causes the column address and the shift register to be reset to 0 and the row address to be shifted by one. Asserting the nxtscan 726 input high causes the row and column addresses to be reset to 0.

In a normal operation, the entire 8K cell array within each bank is scanned. The ADC requires 16 clock cycles to perform a conversion, and 16 such conversions are performed in order to convert an entire row. Thus, each row requires 256 clock cycles (2.0 µs @ 128 MHz).

Figures 10, 11:
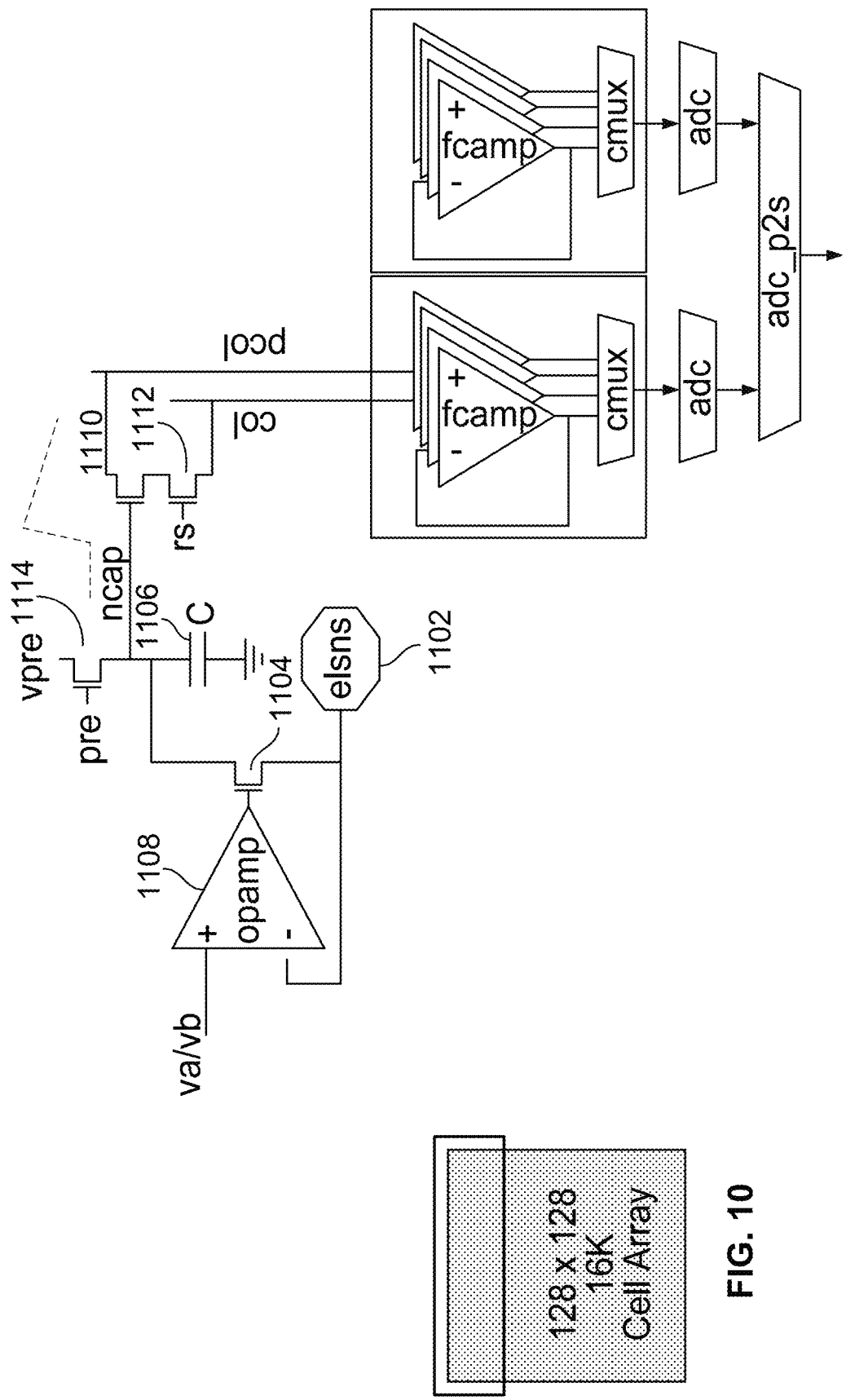
FIG. 10 illustrates that a fraction of the array may be scanned at a time.
FIG. 11 illustrates an embodiment of a circuit for measuring the current in a cell.

Thus, in order to scan the entire 8K cell array, the nxtrow 724 signal is asserted every 256 cycles and the nxtscan 726 signal is asserted for one cycle in every 16,384 cycles. Using a typical clock running at 128 MHz yields a sample rate of 7.8 kHz (128 µs period). It is however possible to tradeoff the number of scanned cells for a higher scan rate by scanning a subset of the array. For example, the top one-quarter of rows of the array may be scanned by asserting the nxtscan 726 signal after 2048 clocks, as shown in FIG. 10. The sampling rate is increased by four times, from ~8 kHz to ~32 kHz. However, the integration time and the voltage signal are reduced by 4 times as well, causing degradation of the signal-to-noise ratio (SNR).

In the above example, one quarter of the array is scanned. However, a larger or a smaller fraction of the array may be scanned at a time. For example, ½ or ⅓ of the rows of the full array may be scanned at a time.

In the above example, three-quarters of the array is left unscanned. In some embodiments, the entire array is scanned in multiple passes. The first pass is as described above. The second pass leaves the nxtrow 724 signal asserted for 16 consecutive clock cycles to bypass the first 16 rows and start a new scan on the $17^{th}$. Scanning of the next quarter of the array is then performed normally before asserting the nxtscan 726 to reset the scan shift registers. The third quarter skips 32 rows and starts scanning on the $33^{rd}$ to scan the final 16 rows.

Thus, by time-interleaving, the entire array is scanned at a much higher rate than normal. The actual sample rate is not improved, since the time required to scan all four quarters of the array does not change. There are effectively "dead times" inserted between each of the quartile scans. In some cases, the current is such that the voltage measurement saturates at the normal 8 kHz scanning rate. Thus, by time-interleaving faster scans, readings of these high current cells in the array are obtained without saturating. The software needs to be cognizant of the precharge signal and perform a double scan of the desired region.

In each cell, current is measured at different applied voltages. The cell includes a circuitry to apply a constant voltage (DC voltage) or an alternating voltage waveform (AC voltage) to the electrode and measure a low level current simultaneously.

In some embodiments, a voltage potential is applied to the liquid contained within a conductive cylinder mounted to the surface of the die. This "liquid" potential is applied to the top side of the pore and is common to all cells in the array. The bottom side of the pore has an exposed electrode, and each sensor cell can apply a distinct bottom side potential to its electrode. The current is measured between the top liquid connection and each cell's electrode connection on the bottom side of the pore. The sensor cell measures the current travelling through the pore as modulated by the molecular complex constricted within the pore.

FIG. 11 illustrates an embodiment of a circuit for measuring the current in a cell. The circuit is electrically connected to an electrochemically active electrode (e.g., AgCl) through an electrode-sense (ELSNS) node 1102. The circuit includes a transistor 1104. Transistor 1104 may be an NMOS or n-channel MOSFET (metal-oxide-semiconductor field-effect transistor) that performs two functions. A controlled voltage potential can be applied to ELSNS node 1102, and the controlled voltage potential can be varied by changing the voltage on the input to an op-amp 1108 controlling transistor 1104, which acts as a source follower. Transistor 1104 also operates as a current conveyer to move electrons from a capacitor 1106 to ELSNS node 1102 (and vice versa). Current from the source pin of transistor 1104 is directly and accurately propagated to its drain pin, accumulating charges on capacitor 1106. Thus, transistor 1104 and capacitor 1106 act together as an ultra-compact integrator (UCI).

The UCI is used to determine the current sourced from or sunk to the electrode by measuring the change in voltage integrated onto capacitor 1106 according to the following:

$$I*t = C*\Delta V$$

where,
 I: Current
 t: integration time
 C: Capacitance
 $\Delta V$: voltage change Typical operation involves precharging capacitor 1106 to a known and fixed value (e.g., $V_{DD}$=1.8 V), and then measuring the voltage change at a fixed interval t. For an 8K bank operating at 128 MHz, each cell integrates for ~128 µs. In one example:

$$C = 5 \ fF$$
$$I = 20 \ pA$$
$$t = 128 \ \mu s$$
$$\Delta V = I*t/C$$
$$= 20 \ pA * 128 \ \mu s / 22 \ fF$$
$$= 512 \ mV$$

In this example, the voltage swing is relatively small, and the resolution of the ADC is on the order of millivolts. The integrated voltage may be increased by reducing the clock rate to less than 128 MHz, thereby increasing the integration period.

In the above circuit, the maximum voltage swing is ~1V, and thus the circuit saturates with a current higher than ~32 pA. The saturation limit can be increased by reducing the scan window to effectively increase the cell scan rate. By interleaving fast and slow scans, the dynamic range of the current that can be measured can be increased.

Transistor 1104 acts as a current conveyor by moving charges from the integrating capacitor 1106 to the electrode. Transistor 1104 also acts as a voltage source, imposing a constant voltage on the electrode through the opamp feedback loop. The column drive transistor 1110 is configured as a source follower in order to buffer the capacitor voltage and provide a low impedance representation of the integrated voltage. This prevents charge sharing from changing the voltage on the capacitor.

Transistor 1112 is a transistor connected to the row select (rs) signal. It is used as a row access device with the analog voltage output at its source connected as a column shared with many other cells. Only a single row of the column connected AOUT signal is enabled so that a single cell voltage is measured.

In an alternative embodiment, the row select transistor (transistor 1112) may be omitted by connecting the drain of the column drive transistor 1110 to a row selectable "switched rail."

A precharge transistor 1114 is used to reset the cell to a predetermined starting voltage from which the voltage is integrated. For example, applying a high voltage (e.g., $V_{DD}$=1.8 V) to both vpre and pre will pull capacitor 1106 up to a precharged value of ($V_{DD}-V_t$). The exact starting value can vary both from cell to cell (due to $V_t$ variation of precharge transistor 1114) as well as from measurement to measurement, due to the reset switch thermal noise (sqrt (kTC) noise). It is possible to eliminate this $V_t$ variation by limiting the precharge voltage to less than $V_{DD}-V_t$. In this case, the precharge transistor 1114 will pull all the way up to the vpre voltage. Even in this case, however, the kT/C noise is still present. As a result, a correlated double sampling (CDS) technique is used to measure the integrator starting voltage and the ending voltage to determine the actual voltage change during the integration period. CDS is accomplished by measuring the voltage on the integrating capacitor 1106 twice: once at the beginning and once at the end of the measurement cycle.

Note also that the drain of precharge transistor 1114 is connected to a controlled voltage vpre (reset voltage). In a normal operation, vpre is driven to a fixed voltage above the electrode voltage. However, it can also be driven to a low voltage. If the vpre node of precharge transistor 1114 is in fact driven to ground, then the current flow is reversed (i.e., current flows from the electrode into the circuit through transistor 1104 and precharge transistor 1114), and the notion of source and drain is swapped. The negative voltage applied to the electrode (with respect to the liquid reference) is controlled by the vpre voltage, assuming that the gate voltages of transistors 1114 and 1104 are at least greater than vpre by a threshold. Thus, a ground voltage on vpre can be used to apply a negative voltage to the electrode, for example to accomplish electroporation or bilayer formation.

An ADC measures the AOUT voltage immediately after reset and again after the integration period (i.e., performs the CDS measurement) in order to determine the current integrated during a fixed period of time. An ADC can be implemented per column. A separate transistor may be used for each column as an analog mux to share a single ADC between multiple columns. The column mux factor can be varied depending on the requirements for noise, accuracy, and throughput.

Figure 12:
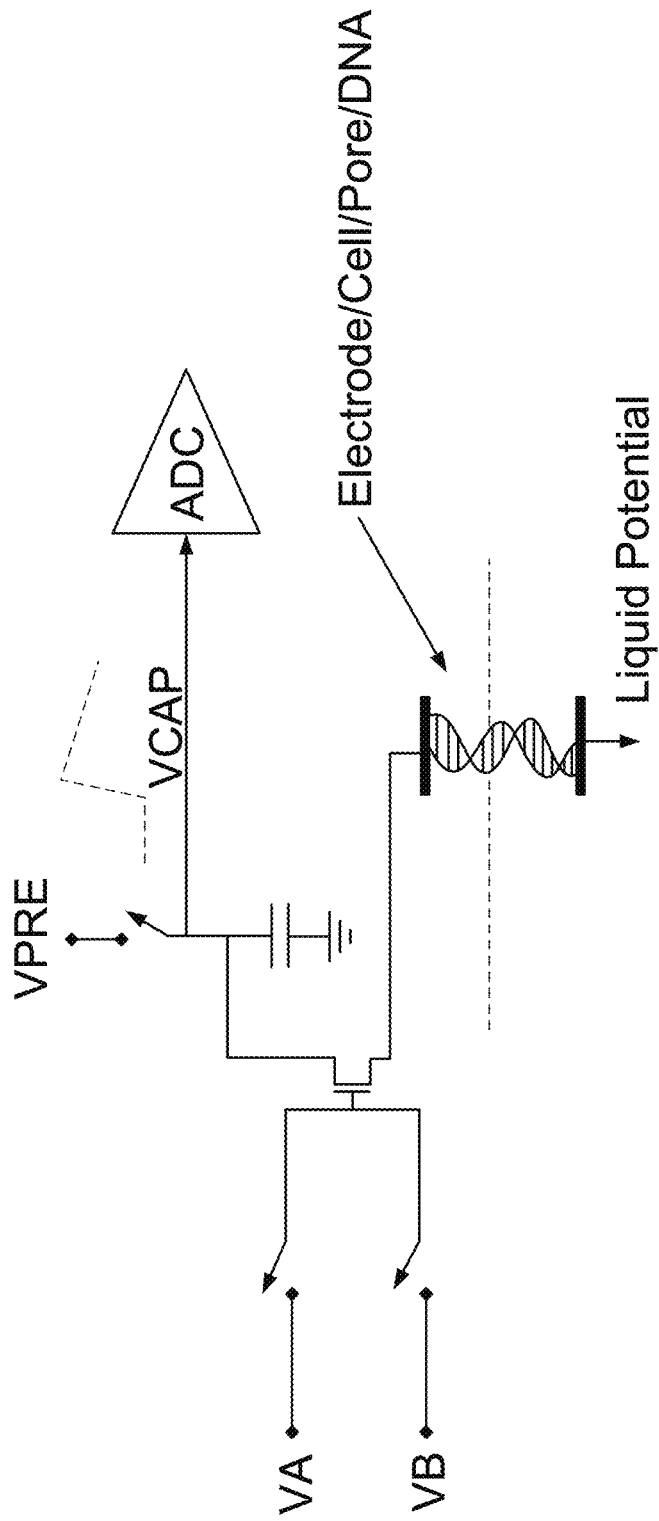
FIG. 12 illustrates an embodiment of a circuit for measuring the current in a cell.

In some alternative embodiments, the op-amp/transistor combination as shown in FIG. 11 may be replaced by a single transistor as shown in FIG. 12.

Figure 13:
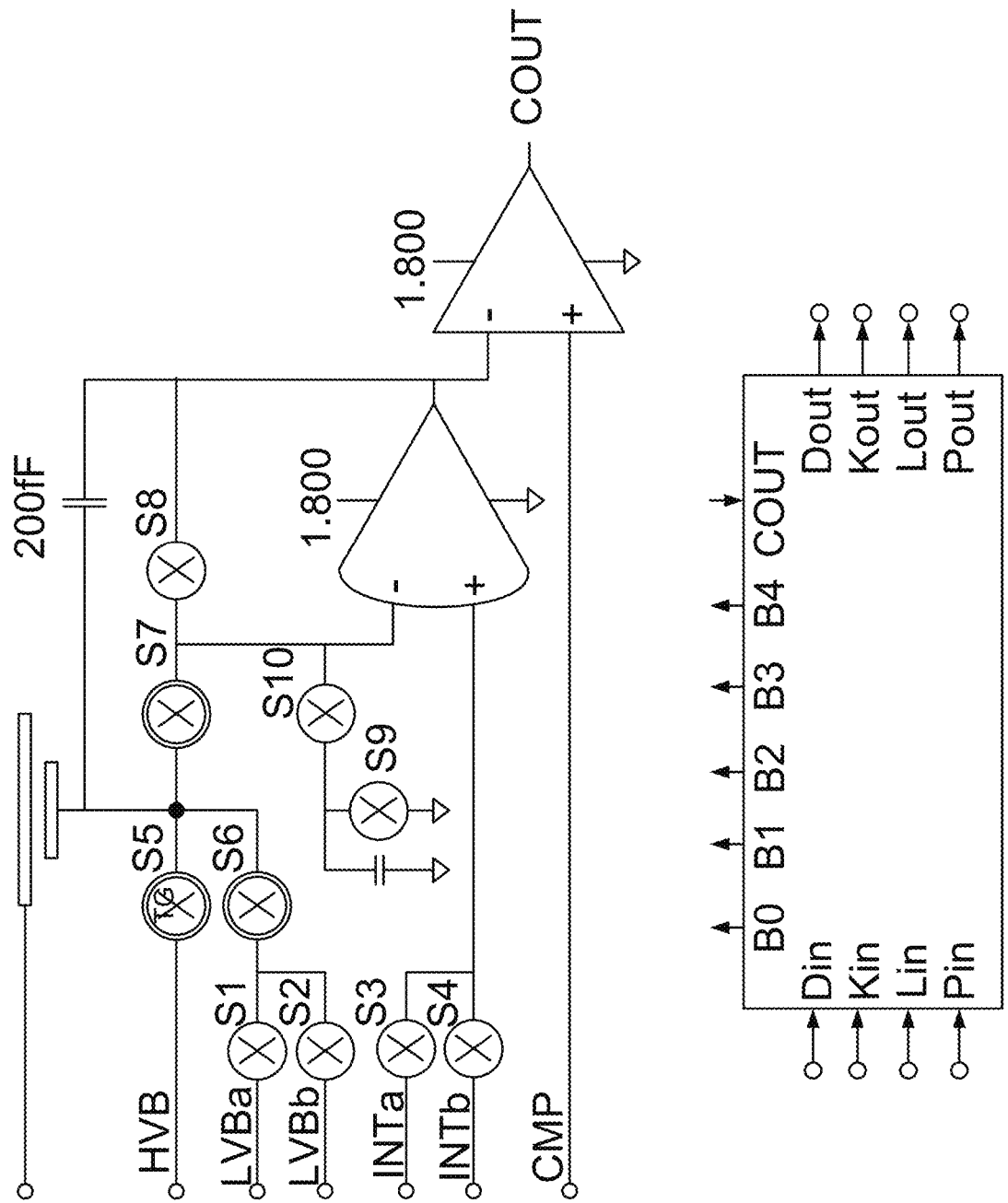
FIG. 13 illustrates an embodiment of a circuit for measuring the current in a cell.

FIG. 13 illustrates an alternative embodiment of a circuit for measuring the current in a cell. The circuit includes an integrator, a comparator, and digital logic to shift in control bits and simultaneously shift out the state of the comparator output. The B0 through B1 lines come out of the shift register. The analog signals are shared by all cells within a bank, and the digital lines are daisy-chained from cell to cell.

The cell digital logics include a 5 bit data shift register (DSR), 5 bit parallel load registers (PLR), control logic, and an analog integrator circuit. Using the LIN signal, the control data shifted into the DSR is loaded in parallel into the PLR. The 5 bits control digital "break-before-make" timing logic controls the switches in the cell. The digital logic has a set-reset (SR) latch to record the switching of the comparator output.

The architecture in FIG. 13 delivers a variable sample rate that is proportional to the individual cell current. A higher current results in more samples per second than a lower current. The resolution of the current measurement is related to the current being measured. A small current is measured with a finer resolution than a large current, which is a clear benefit over fixed resolution measurement systems. An analog input may be used to adjust sample rates by changing the voltage swing of the integrator. Thus, it is possible to increase the sample rate in order to analyze biologically fast processes or to slow the sample rate (thereby gaining precision) in order to analyze biologically slow processes.

The output of the integrator is initialized to a low voltage bias (LVB) and integrates up to a voltage CMP. A sample is generated every time the integrator output swings between these two levels. Thus, the greater the current, the faster the integrator output swings and therefore the faster the sample rate. Similarly, if the CMP voltage is reduced, the output swing of the integrator needed to generate a new sample is reduced and therefore the sample rate is increased. Thus, simply reducing the voltage difference between LVB and CMP provides a mechanism to increase the sample rate.

Using the architecture as shown in FIG. 13, an integrator and a comparator are used at each cell site. The current being measured is integrated, creating a voltage ramp at the output of the integrator. When this voltage reaches a predetermined value (the comparator threshold), a flag is sent to a circuitry on the periphery of the array. The number of clock pulses counted between the initiation of the integrator ramp and the tripping of the comparator is a measure of the current value. The conversion time is thus a variable.

Using the architecture as shown in FIG. 11, the integrator ramps for a configurable fixed period of time. At the beginning and at the end of that time, an ADC on the periphery of the array measures the voltage. Advantages of the architecture in FIG. 11 include: 1) The amount of circuitry at each site is less because there is no comparator; and 2) Having a configurable fixed conversion time is desirable when dealing with large amount of data generated by denser arrays (e.g., 100,000 to 1,000,000 sites or more).

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A device, the device comprising:
    a precharging voltage source;
    a first cell electrode;
    a second electrode, the second electrode configured to apply a liquid potential to a liquid in contact with a nanopore positioned electrically between the first cell electrode and the second electrode;
    a capacitor electronically coupled to the first cell electrode;
    an electronic switch that selectively couples the capacitor to the precharging voltage source;
    an analog-to-digital converter electrically coupled to the capacitor; and
    a processor programmed to:
        send a precharge signal to the electronic switch to close the electronic switch and electrically couple the capacitor to the precharging voltage source;
        precharge the capacitor to a set voltage at a beginning of a measurement period;
        send a signal to the electronic switch to open the electronic switch to decouple the capacitor from the precharging voltage source; and
        measure a decay in voltage across the capacitor during the measurement period using the analog-to-digital converter.

2. The device of claim 1, further comprising a liquid chamber containing the liquid.

3. The device of claim 2, wherein
    the second electrode supplies the liquid potential when the liquid chamber contains an electrolyte;
    the first cell electrode supplies a variable electric potential when the liquid chamber contains the electrolyte, wherein a voltage between the second electrode and the first cell electrode equals the variable electric potential minus the liquid potential; and
    the decay in voltage across the capacitor is a function of a resistance through the nanopore.

4. The device of claim 3, wherein,
    the device is configured to detect a physical state and transpose the physical state from a plurality of possible physical states of a material in the liquid chamber, by modulating the voltage between the second electrode and the first cell electrode and measuring a voltage decay between the first cell electrode and the second electrode, and
    the plurality of possible physical states comprises:
        no formation of a lipid bilayer,
        formation of a lipid bilayer,
        insertion of a nanopore protein in a lipid bilayer, forming a nanopore, and
        interaction of a molecular complex with the nanopore.

5. The device of claim 2, wherein the device is configured to retain at least one lipid, one nanopore protein, and one molecular complex in the liquid chamber.

6. The device of claim 5, wherein the device is configured to recognize a specific base type corresponding to the molecular complex in the liquid chamber by using the measurement of the decay in voltage across the capacitor.

7. The device of claim 1, further comprising
    a buffering component that is electrically coupled to the analog-do-digital converter to buffer an output of the capacitor before being connected to the analog-do-digital converter.

8. The device of claim 1, wherein the analog-to-digital converter electrically coupled to the capacitor measures a first voltage at an output of the capacitor at the beginning of the measurement period and a second voltage at the output of the capacitor at an end of the measurement period, and wherein a difference of the second voltage and the first voltage corresponds to the measurement of the decay in voltage across the capacitor.

9. The device of claim 8, wherein the measurement period is set or predetermined and remains fixed between measurements.

10. The device of claim 1, wherein the analog-to-digital converter includes a comparator.

11. The device of claim 10, wherein the analog-to-digital converter includes a controlling analog input, and the controlling analog input controls a variable sample rate of a current flowing between the first cell electrode and the second electrode by varying a voltage at the controlling analog input.

12. The device of claim 11, wherein the variable sample rate increases when the current flowing between the first cell electrode and the second electrode increases.

13. The device of claim 11, wherein the varied voltage comprises a comparator threshold.

14. The device of claim 11, wherein the varied voltage comprises an initial voltage at an output of the capacitor.

15. A device, the device comprising:
a precharging voltage source;
a first cell electrode;
a second electrode, the second electrode configured to apply a liquid potential to a liquid in contact with a nanopore positioned electrically between the first cell electrode and the second electrode;
a capacitor electronically coupled to the first cell electrode;
an electronic switch that selectively couples the capacitor to the precharging voltage source;
an analog-to-digital converter electrically coupled to the capacitor; and
a processor programmed to:
send a precharge signal to the electronic switch to close the electronic switch and electrically couple the capacitor to the precharging voltage source;
precharge the capacitor to a set voltage at a beginning of a measurement period;
send a signal to the electronic switch to open the electronic switch to decouple the capacitor from the precharging voltage source; and
measure a decay in voltage across the capacitor during the measurement period using the analog-to-digital converter, wherein the measurement period is set or predetermined and remains fixed between measurements.

16. A device, the device comprising:
a precharging voltage source;
a first cell electrode;
a second electrode, the second electrode configured to apply a liquid potential to a liquid in contact with a nanopore positioned electrically between the first cell electrode and the second electrode;
a capacitor electronically coupled to the first cell electrode;
an electronic switch that selectively couples the capacitor to the precharging voltage source;
an analog-to-digital converter electrically coupled to the capacitor; and
a processor programmed to:
send a precharge signal to the electronic switch to close the electronic switch and electrically couple the capacitor to the precharging voltage source;
precharge the capacitor to a set voltage at a beginning of a measurement period;
send a signal to the electronic switch to open the electronic switch to decouple the capacitor from the precharging voltage source; and
measure a decay in voltage across the capacitor during the measurement period using the analog-to-digital converter, wherein the measurement period is determined based on a time for the measured decay in voltage across the capacitor to reach a fixed magnitude.

* * * * *